(12) United States Patent
Wang et al.

(10) Patent No.: US 7,589,837 B2
(45) Date of Patent: Sep. 15, 2009

(54) MULTIPLE TILE CALIBRATION METHOD FOR COLOR SENSORS

(75) Inventors: Yao Rong Wang, Webster, NY (US); Lalit Keshav Mestha, Fairport, NY (US); Peter Michael Gulvin, Webster, NY (US); Pinyen Lin, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 405 days.

(21) Appl. No.: 11/606,985

(22) Filed: Dec. 1, 2006

(65) Prior Publication Data

US 2008/0130009 A1    Jun. 5, 2008

(51) Int. Cl.
*G01J 3/46* (2006.01)
(52) U.S. Cl. .................... 356/402; 250/252.1
(58) Field of Classification Search ............. 250/252.1; 356/402
See application file for complete search history.

(56) References Cited

U.S. PATENT DOCUMENTS

| 6,295,130 | B1 |   | 9/2001  | Sun et al.    |         |
|-----------|----|---|---------|---------------|---------|
| 6,542,185 | B1 | * | 4/2003  | Bogardus      | 348/223.1 |
| 6,556,932 | B1 | * | 4/2003  | Mestha et al. | 702/76  |
| 6,721,692 | B2 |   | 4/2004  | Mestha et al. |         |
| 6,876,448 | B2 | * | 4/2005  | Imura et al.  | 356/326 |
| 2006/0221346 | A1 |   | 10/2006 | Mestha et al. |      |
| 2007/0260413 | A1 | * | 11/2007 | Ehbets et al. | 702/104 |
| 2008/0080026 | A1 |   | 4/2008  | Mestha et al. |      |

* cited by examiner

*Primary Examiner*—Kara E Geisel
(74) *Attorney, Agent, or Firm*—Pillsbury Winthrop Shaw Pittman LLP

(57) ABSTRACT

A new calibration method for a spectrophotometer or a color sensor is provided using multiple color tiles with known reflectances. This procedure uses multiple reference standard tiles, in addition to, the standard white tile and substitutes a wavelength dependent adjustment constant instead of the dark noise reading. The constant is computed using measurements of multiple reference tiles with known reflectance spectra, and its purpose is to weight the sensor readings in order to avoid ill-posed scaling caused by physical limitations such as less than ideal light sources. A scaling factor may be calculated and also used to compute the reflectance of an arbitrary object. A device for carrying out the method is also provided.

18 Claims, 3 Drawing Sheets

MULTIPLE TILE CALIBRATION METHOD FOR COLOR SENSORS

FIELD

The present application relates to a calibration method for a spectrophotometer or a color sensor using multiple color tiles with known reflectances.

BACKGROUND

A spectrophotometer measures the reflectance of an illuminated object of interest over many wavelengths. Typically, a spectrophotometer uses 16 to 36 channels to cover the wavelengths between 380 nm to 780 nm, within the human visible spectral range. One example is the MEMS Fabry-Perot spectrophotometer as an array color sensor with tunable wavelengths as described in detail in U.S. Pat. No. 6,295,130, and U.S. patent application Ser. No. 11/535,382, filed Sep. 26, 2006, entitled "MEMS Fabry-Perot Inline Color Scanner For Printing Applications Using Stationary Membranes," which are incorporated herein by reference.

FIG. 1 shows the basic structure of a Fabry-Perot spectrophotometer. The spectrophotometer 100 is preferably fabricated using semiconductor microelectromechanical system (MEMS) processing techniques with a photodetector 175, and a Fabry-Perot cavity filter 110 monolithically integrated on a substrate 185 that is typically silicon. Silicon wafer 190 is aligned over the silicon wafer 185 and the Fabry-Perot filter 110 using a flip-chip pick and drop aligner. Optical fiber 199 is inserted into a circular hole 195 and epoxied to silicon wafer 190.

The cavity filter 110 includes two micro-mirrors 120, 130 separated by a gap 125. The gap 125 may be an air gap, or may be filled with a liquid or other dielectric material. The micro-mirrors 120, 130 include multi-layer distributed Bragg reflector (DBR) stacks 115 of highly reflective metallic layers, such as gold. A voltage applied between the two mirrors across transparent electrodes 135, 140 may be adjusted to change a dimension d of a gap, such as a size of the gap. Only light incident normal to the micro-mirror with wavelengths near, $$\lambda = 2nd/m \text{ with } m=1,2,3 \ldots \quad (1)$$

will be able to pass the gap and reach the photodetector 175 due to interference effect of incident light and reflective light within the gap.

In Eq. (1), n represents the refractive index of the gap material (n=1 for air), and d is the gap distance.

Usually, a spectrophotometer is calibrated by measuring the spectra of a standard white tile with known reflectance. A scaling factor used to calibrate the sensor is given by $$f(\lambda) = \frac{R_w(\lambda)}{V_w(\lambda) - D(\lambda)} \quad (2)$$

where $R_w(\lambda)$ is the reflectance of the white tile, $V_w(\lambda)$ is the sensor measurement for the white tile, and $D(\lambda)$ is the dark reading of the sensor. The reflectance $R(\lambda)$ of an arbitrary object with $V(\lambda)$ as the unscaled measured reflectance by the sensor is given by $$R(\lambda) = [V(\lambda) - D(\lambda)]f(\lambda) \quad (3)$$

FIG. 2 shows the method used for the conventional white tile calibration procedure. Beginning at step 2000, the process continues to step 2001, where white tile measurements from the sensor $V_w(\lambda)$ at each wavelength $\lambda$ are obtained. The process then continues to step 2002 where the dark reading $D(\lambda)$ of the sensor is measured. Continuing to step 2003, the scaling factor $f(\lambda)$ is calculated according to Eq. (2).

In step 2004 measurements $V(\lambda)$ of an arbitrary object at each wavelength $\lambda$ are obtained using the sensor. Next, in step 2005 the reflectance $R(\lambda)$ of the object is computed according to Eq. (3). Continuing to step 2006, a determination is made whether a further object is to be measured. If not, the process continues to step 2007. Otherwise, the process steps 2004, 2005 and 2006 may be repeated, as necessary, for a plurality of object measurements. Finally, the process ends in step 2007.

There are a few potential problems, however, that can cause inaccuracies with this calibration procedure. They are:

(1) The dark reading may not be accurate and is generally noisy due to low signal levels.

(2) The accuracy of the sensor measurement at a given wavelength may vary. For the example of the MEMS Fabry-Perot sensor, the accuracy depends on the uniformity of the gap between Fabry-Perot cavity reflectors. The deviation of the gap from the nominal value as given in Eq. (1) may also result in an inaccurate reading.

(3) Noise or deficiency in a part of the spectra of the light source may also introduce inaccuracy in the sensor output. For example, if the light source is deficient at the blue end, the measurements $V_w(\lambda)$ and $V(\lambda)$ in Eq. (2) and Eq. (3) may be equal to or even smaller than the dark reading $D(\lambda)$ for the blue lights, creating the situation that the reflectance obtained from this calibration method becomes unreliable. This situation happens quite often in real practice. Better blue light sources, specifically blue LEDs, are now becoming available. However, such light sources may not always be available or may even be too expensive to instrument in a low cost sensor.

(4) Structural differences/variations during manufacture between multiple pixel elements can lead to pixel-to-pixel measurement variation.

Thus, there is a need for an improved calibration procedure to further improve the sensor accuracy performance in the presence of these problems and many unknown structural and procedural defects in color sensor.

SUMMARY

A new calibration method for a color sensor is provided using multiple color tiles with known reflectances. This procedure uses multiple reference color tiles in addition to the standard white tile and substitutes a wavelength dependent adjustment constant instead of the dark reading of the sensor. The wavelength dependent adjustment constant is computed using measurements of multiple reference tiles with known reflectance spectra, and its purpose is to weight the sensor readings in order to avoid ill-posed scaling caused by physical limitations, such as less than ideal light sources. A scaling factor may be calculated and later used to compute the reflectance of an arbitrary object.

The method can be applied to existing spectrophotometers or colorimeters such as the low-cost LED (LCLED) color sensor or Full-Width-Array RGB scanner as well as a new class of array spectrophotometers such as the MEMS. Fabry-Perot spectrophotometer.

Other objects, features, and advantages of one or more embodiments of the present invention will seem apparent from the following detailed description, the accompanying drawings, and the appended claims.

BRIEF DESCRIPTION OF THE DRAWINGS

Embodiments of the present invention will now be disclosed, by way of example only, with reference to the accompanying schematic drawings in which corresponding reference symbols indicate corresponding parts, in which.

DETAILED DESCRIPTION

Figure 1:
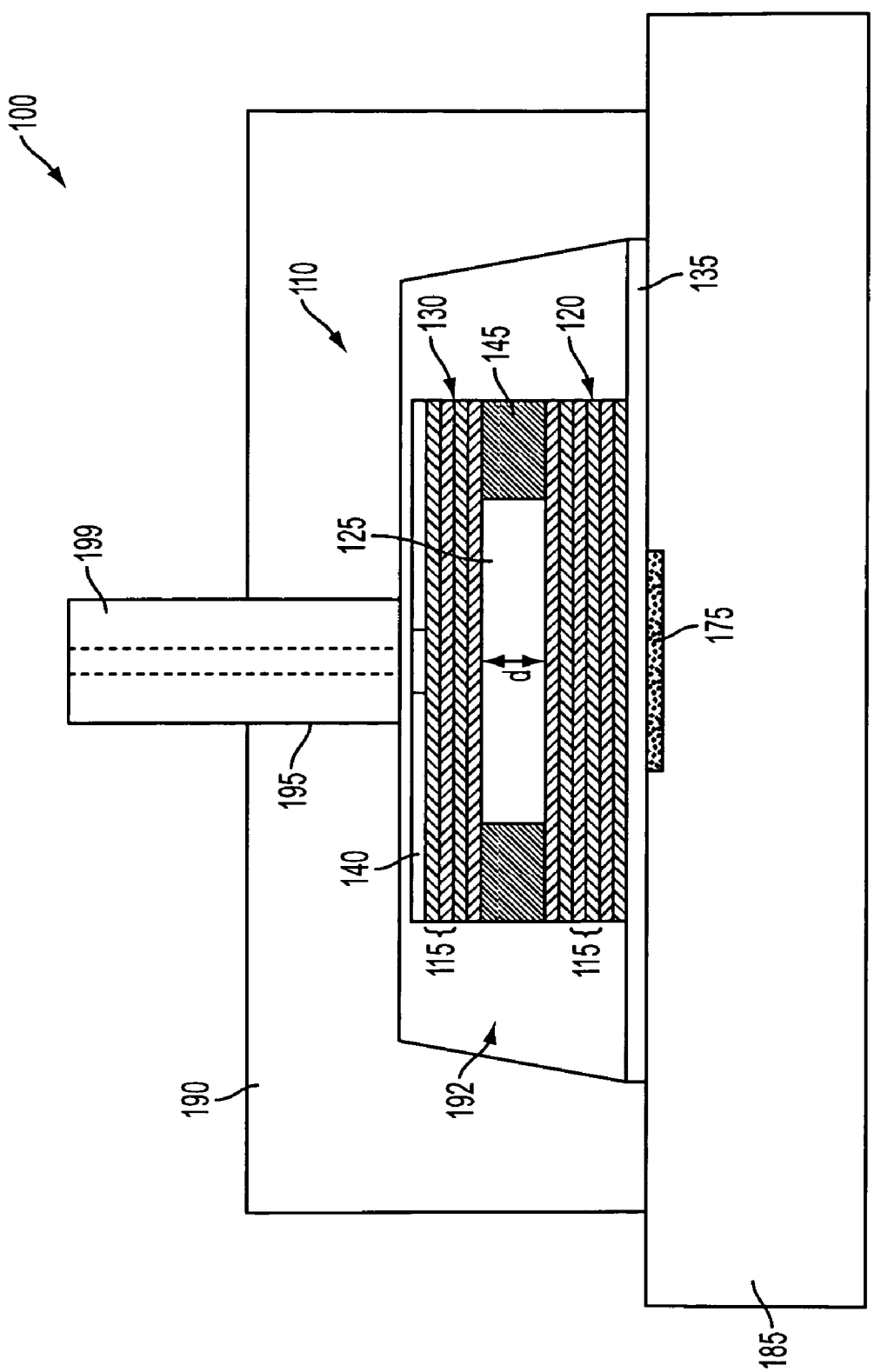
FIG. 1 shows a Fabry-Perot spectrophotometer, which may be calibrated in accordance with the present invention.

FIG. 1 shows a Fabry-Perot spectrophotometer that may be calibrated in accordance with the present invention. The illustrated Fabry-Perot spectrophotometer is provided solely as an example, and should not be regarded as limiting. To the contrary, the method can be applied to any existing spectrophotometer, calorimeter, sensor, or scanner. For example, the method may be practiced using low-cost LED (LCLED) color sensors or Full-Width-Array RGB scanners.

The proposed new calibration method uses two or more color tiles in addition to the standard white tile with known reflectance spectra. Such tiles are available commercially, such as BCRA tiles. Each color tile is colored differently from one other. Assuming that the sensor output V has to be adjusted or scaled for each wavelength, and that there are m color tiles available with known reflectance spectra in addition to the white tile, the adjustment to the scaling factor in Eq. (2) for each wavelength is given by $$f(\lambda) = \frac{R_w(\lambda)}{V_w(\lambda) + A(\lambda)} \qquad (4)$$

where $A(\lambda)$ is a wavelength dependent adjustable constant that will be determined later using the multiple tile calibration method. For the i th standard tile (i=1, 2, ... m) with the known reflectance $R_i(\lambda)$ for each wavelength the measured reflectance $r_i(\lambda)$ will be $$r_i(\lambda) = [V_i(\lambda) + A(\lambda)] f(\lambda) \qquad (5)$$

A solution can be obtained by minimizing the error $$J = \sum_{i=1}^{m} (R_i(\lambda) - r_i(\lambda))^2$$

with respect to $A(\lambda)$. Unlike the usual least square minimization, Eqs. (4) and (5) are non-linear with respect to $A(\lambda)$. However, a unique closed form solution can be obtained in this case. Thus, we have:

$$A(\lambda) = \frac{V_w(\lambda) X_1(\lambda) - X_2(\lambda)}{X_1(\lambda) - V_w(\lambda) X_3(\lambda)} \qquad (6)$$

where $$X_1(\lambda) = \sum_{i=1}^{m} (R_i(\lambda) - R_w(\lambda))(R_i(\lambda) V_w(\lambda) - V_i(\lambda) R_w(\lambda)) \qquad (7)$$

$$X_2(\lambda) = \sum_{i=1}^{m} (R_i(\lambda) V_w(\lambda) - V_i(\lambda) R_w(\lambda))^2 \qquad (8)$$

$$X_3(\lambda) = \sum_{i=1}^{m} (R_i(\lambda) - R_w(\lambda))^2 \qquad (9)$$

Once $A(\lambda)$ is determined, the reflectance spectra $R(\lambda)$ of any object can be obtained using the following equation from the sensor measurement $V(\lambda)$:

$$R(\lambda) = [V(\lambda) + A(\lambda)] f(\lambda) \qquad (10)$$

This equation is similar to Eq. 3, but is written with the wavelength dependent adjustable constant $A(\lambda)$ instead of the dark reading $D(\lambda)$ of the sensor.

If the sensor is specialized for measuring a particular class of materials, such as the xerographic color gamut of a set of printers, and a large data base of reflectances for the class of materials is available, further calibration using the database after the multiple tiles calibration can be applied for improvement as detailed in U.S. Pat. No. 6,721,692, which is incorporated herein by reference.

If 'ij' represent the detector elements along i=1, 2, 3, ... N rows and j=1, 2, 3 ... M columns of a full width array based MEMS or RGB color sensor scans, then Eq. 10 is further modified to scale the output of each detector element as follows:

$$R_{ij}(\lambda) = [V_{ij}(\lambda) + A_{ij}(\lambda)] f_{ij}(\lambda) \qquad (11)$$

Figure 2:
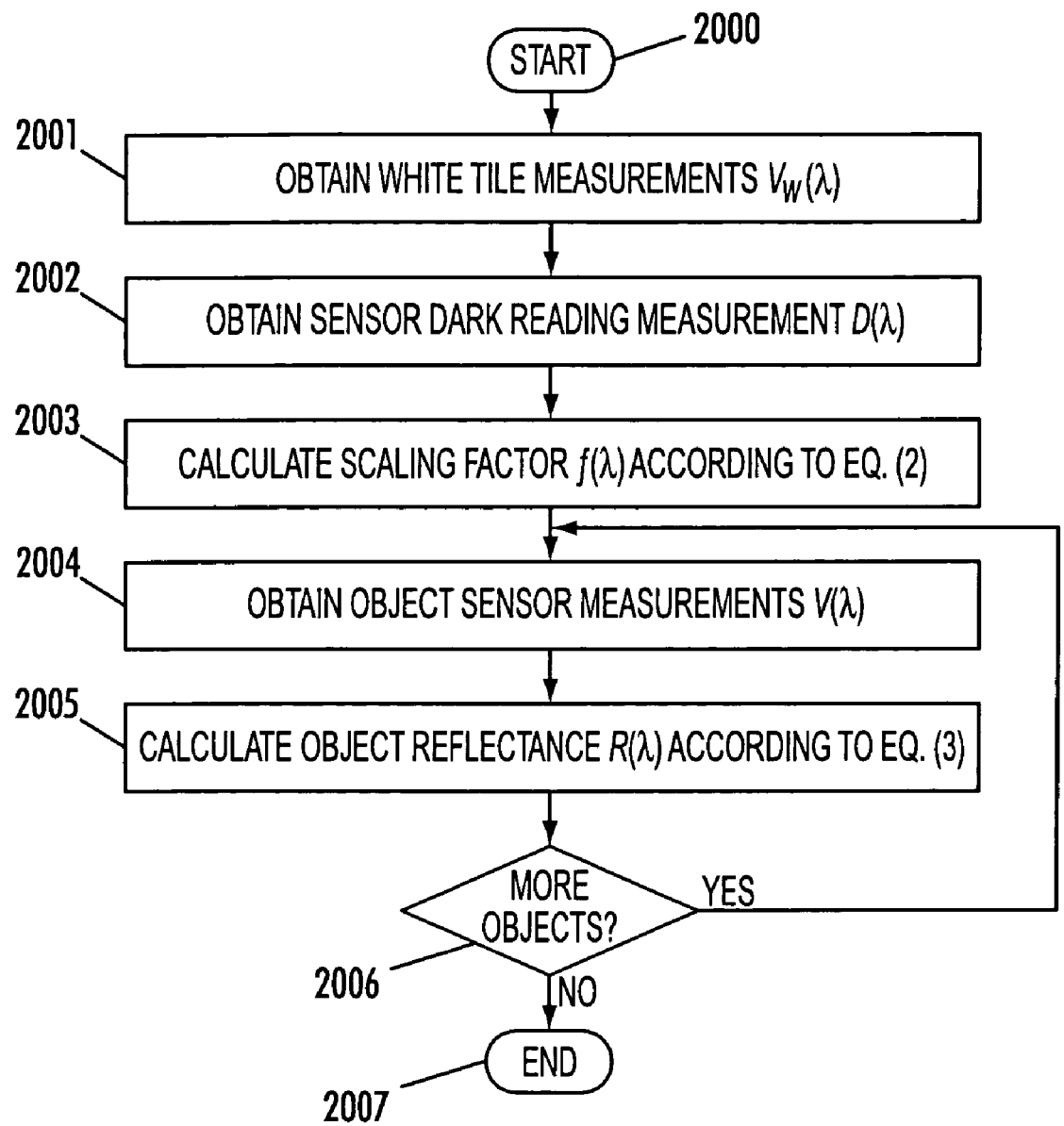
FIG. 2 is a functional block diagram illustration of a conventional white tile calibration method.
Figure 3:
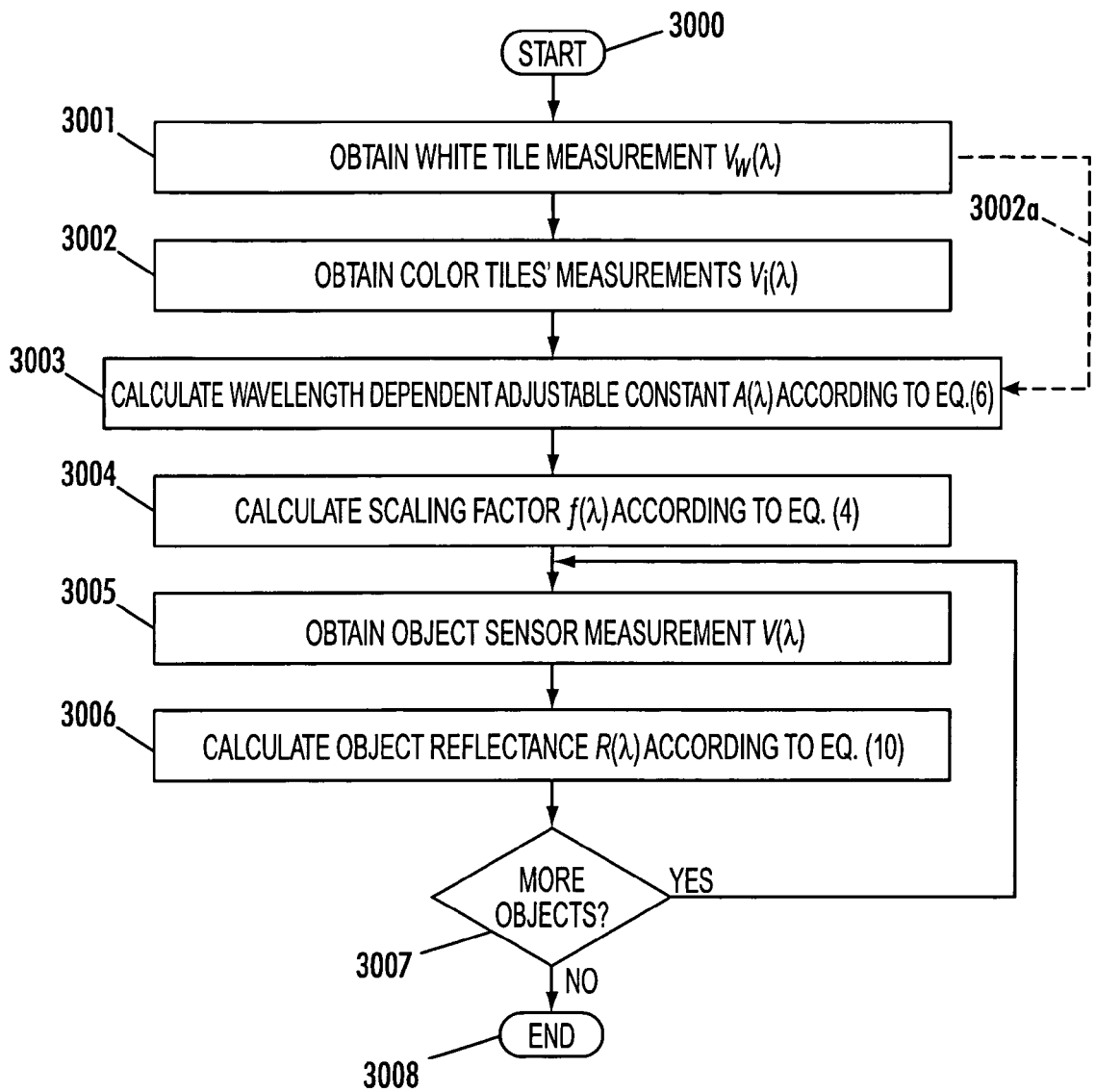
FIG. 3 is a functional block diagram illustration of an exemplary embodiment of the multiple tile calibration method in accordance with the present invention.

FIG. 3 shows the multiple tile calibration procedure in accordance with an embodiment of the present invention. Beginning at step 3000, the process continues to step 3001, where white tile measurements from the sensor $V_w(\lambda)$ at each wavelength $\lambda$ are obtained. This step is essentially the same as step 2001 in FIG. 2. The process then continues to step 3002 where the measurements of the color tiles with known spectra from the sensor $V_i$ at each wavelength $\lambda$ are obtained. Continuing to step 3003, the wavelength dependent adjustable constant $A(\lambda)$ is calculated according to Eq. (6) and stored. Next in step 3004, the scaling factor $f(\lambda)$ is calculated according to Eq. (4). The calculations of $A(\lambda)$ and $f(\lambda)$ can be coded inside the sensor hardware. In other embodiments, these calculations can also be performed in the control/image processing computer to scale the sensor outputs.

In step 3005, using the sensor an arbitrary object measurements $V(\lambda)$ at each wavelength $\lambda$ are obtained. Next, in step 3006 the reflectance $R(\lambda)$ of the arbitrary object is computed according to Eq. (10). Continuing to step 3007, a determination is made whether a further object is to be measured. If not, the process continues to step 3008. Otherwise, the process steps 3005, 3006 and 3007 may be repeated, as necessary, for a plurality of detector elements, ij, and arbitrary object measurements. Finally, the process ends in step 3008.

It is not necessary that the color tiles measurements be frequently updated to compute the scaling factor, unless the sensor is old and/or requires further adjustment to the scaling factor. Therefore, whenever a new calibration is required, bypass step 3002a is optionally proposed, to use the white tile measurement 3001 with previously stored color tile measurements to calculate the wavelength dependent adjustable constant $A(\lambda)$ in step 3003, thus skipping step 3002.

Test results, thus far, have indicated that the color sensing error (as measured by deltaE2000) for the multiple tile calibration method is reduced by nearly a factor of 2 compared to the conventional white tile calibration method.

Any patents referred to in this application, including any in the Background section, are incorporated into the present invention.

While the specific embodiments of the present invention have been described above, it will be appreciated that the invention may be practiced otherwise than described. The description is not intended to limit the invention.

What is claimed is:

1. A method for calculating a scaling factor for a sensor, comprising:
   (a) providing a white tile with known reflectance $R_w(\lambda)$ over a spectra having wavelengths $\lambda$;
   (b) providing two or more color tiles with known reflectance $R_i(\lambda)$ over said spectra;
   (c) obtaining, via the sensor, measurements $V_w(\lambda)$ for the reflectance of said white tile at each wavelength of said spectra;
   (d) obtaining, via the sensor, measurements $V_i(\lambda)$ for the reflectance of each of said color tiles at each wavelength of said spectra;
   (e) calculating a wavelength dependent adjustable constant $A(\lambda)$ for each wavelength of said spectra as a function of $R_w(\lambda)$ and $V_w(\lambda)$ for said white tile and $R_i(\lambda)$ and $V_i(\lambda)$ for each of said color tiles; and
   (f) calculating a scaling factor $f(\lambda)$ for each wavelength of said spectra, as follows:

$$f(\lambda) = \frac{R_w(\lambda)}{V_w(\lambda) + A(\lambda)}.$$

2. The method of claim 1, wherein in step (e) the wavelength dependent adjustable constant for each wavelength of the spectra is calculated as follows:

$$A(\lambda) = \frac{V_w(\lambda)X_1(\lambda) - X_2(\lambda)}{X_1(\lambda) - V_w(\lambda)X_3(\lambda)}$$

where $$X_1(\lambda) = \sum_{i=1}^{m}(R_i(\lambda) - R_w(\lambda))(R_i(\lambda)V_w(\lambda) - V_i(\lambda)R_w(\lambda))$$

$$X_2(\lambda) = \sum_{i=1}^{m}(R_i(\lambda)V_w(\lambda) - V_i(\lambda)R_w(\lambda))^2$$

$$X_3(\lambda) = \sum_{i=1}^{m}(R_i(\lambda) - R_w(\lambda))^2$$

m=the number of color tiles.

3. The method of claim 1, further comprising:
   (g) obtaining sensor measurements $V(\lambda)$ for the reflectance of an object at each wavelength of said spectra;
   (h) calculating the reflectance $R(\lambda)$ of said object as follow:

$R(\lambda) = [V(\lambda) + A(\lambda)]f(\lambda)$; and (i) repeating steps (g) and (h), as necessary, for a plurality of objects.

4. The method of claim 1, wherein said wavelengths are between 380 nm to 780 nm.

5. The method of claim 1, wherein said sensor is selected from the group consisting of a spectrophotometer, a Fabry-Perot spectrophotometer, a colorimeter, a low-cost LED (LCLED) color sensor, and a Full-Width-Array RGB scanner.

6. The method of claim 1, wherein said sensor is part of a xerographic system.

7. The method of claim 1, wherein said white tile and/or said color tiles are BCRA tiles.

8. The method of claim 1, wherein said calculations are performed by sensor hardware.

9. A method for calculating a scaling factor for a sensor, comprising:
   (a) providing a white tile with known reflectance $R_w(\lambda)$ over a spectra having wavelengths $\lambda$;
   (b) providing two or more color tiles with known reflectance $R_i(\lambda)$ over said spectra;
   (c) obtaining sensor measurements $V_w(\lambda)$ for the reflectance of said white tile at each wavelength of said spectra;
   (d) obtaining sensor measurements $V_i(\lambda)$ for the reflectance of each of said color tiles at each wavelength of said spectra;
   (e) calculating a wavelength dependent adjustable constant $A(\lambda)$ for each wavelength of said spectra as a function of $R_w(\lambda)$ and $V_w(\lambda)$ for said white tile and $R_i(\lambda)$ and $V_i(\lambda)$ for each of said color tiles; and
   (f) calculating a scaling factor $f(\lambda)$ for each wavelength of said spectra, as follows:

$$f(\lambda) = \frac{R_w(\lambda)}{V_w(\lambda) + A(\lambda)},$$

wherein said calculations are performed using a control/image processing computer.

10. The method of claim 1, wherein a plurality of said sensors are provided in an array such that said calibration factor is calculated for each sensor.

11. The method of claim 1, further comprising recalculating said scaling factor by using previously stored measurements of said color tiles.

12. A method for calibrating a sensor, comprising:
   (a) providing a white tile with known reflectance $R_w(\lambda)$ over a spectra having wavelengths $\lambda$;
   (b) providing two or more color tiles with known reflectance $R_i(\lambda)$ over said spectra;
   (c) obtaining, via the sensor, measurements $V_w(\lambda)$ for the reflectance of said white tile at each wavelength of said spectra;
   (d) obtaining, via the sensor, measurements $V_i(\lambda)$ for the reflectance of each of said color tiles at each wavelength of said spectra;
   (e) calculating, via a processor, a wavelength dependent adjustable constant $A(\lambda)$ for each wavelength of said spectra as follows:

$$A(\lambda) = \frac{V_w(\lambda)X_1(\lambda) - X_2(\lambda)}{X_1(\lambda) - V_w(\lambda)X_3(\lambda)}$$

where $$X_1(\lambda) = \sum_{i=1}^{m}(R_i(\lambda) - R_w(\lambda))(R_i(\lambda)V_w(\lambda) - V_i(\lambda)R_w(\lambda))$$

$$X_2(\lambda) = \sum_{i=1}^{m}(R_i(\lambda)V_w(\lambda) - V_i(\lambda)R_w(\lambda))^2$$

-continued $$X_3(\lambda) = \sum_{i=1}^{m}(R_i(\lambda) - R_w(\lambda))^2$$

m=the number of color tiles; and (f) calculating, via the processor, a scaling factor $f(\lambda)$ for each wavelength of said spectra, as follows:

$$f(\lambda) = \frac{R_w(\lambda)}{V_w(\lambda) + A(\lambda)}$$

(g) obtaining, via the sensor, measurements $V(\lambda)$ of an object at each wavelength of said spectra;

(h) calculating, via the processor, the reflectance $R(\lambda)$ of said object as follow:

$R(\lambda)=[V(\lambda)+A(\lambda)]f(\lambda)$; and (i) repeating steps (g) and (h), as necessary, for a plurality of objects.

13. A sensor calibrating system comprising:

(a) a sensor configured to:
  (1) obtain measurements $V_w(\lambda)$ from a white tile with known reflectance $R_w(\lambda)$ over a spectra having wavelengths $\lambda$, at each wavelength of said spectra; and
  (2) obtain measurements $V_i(\lambda)$ from at least two color tiles with known reflectance $R_i(\lambda)$ over said spectra having wavelengths, at each wavelength of said spectra;

(b) a device for calculating a wavelength dependent adjustable constant $A(\lambda)$ for each wavelength of said spectra as a function of $R_w(\lambda)$ and $V_w(\lambda)$ for said white tile and $R_i(\lambda)$ and $V_i(\lambda)$ for each of said color tiles; and (c) a device for calculating a scaling factor $f(\lambda)$ for each wavelength of said spectra, as follows:

$$f(\lambda) = \frac{R_w(\lambda)}{V_w(\lambda) + A(\lambda)}.$$

14. The system of claim 13, wherein step (b) is calculated as follows:

$$A(\lambda) = \frac{V_w(\lambda)X_1(\lambda) - X_2(\lambda)}{X_1(\lambda) - V_w(\lambda)X_3(\lambda)}$$

where $$X_1(\lambda) = \sum_{i=1}^{m}(R_i(\lambda) - R_w(\lambda))(R_i(\lambda)V_w(\lambda) - V_i(\lambda)R_w(\lambda))$$

$$X_2(\lambda) = \sum_{i=1}^{m}(R_i(\lambda)V_w(\lambda) - V_i(\lambda)R_w(\lambda))^2$$

$$X_3(\lambda) = \sum_{i=1}^{m}(R_i(\lambda) - R_w(\lambda))^2$$

m=the number of color tiles.

15. The system of claim 13, wherein said sensor is adapted for obtaining sensor measurements $V(\lambda)$ for the reflectance of an object at each wavelength of said spectra.

16. The system of claim 13, further comprising:
a device for calculating reflectance $R(\lambda)$ of an object, as follows:

$R(\lambda)=[V(\lambda)+A(\lambda)]f(\lambda).$

17. The system of claim 13, wherein said wavelengths are between 380 nm to 780 nm.

18. The system of claim 13, wherein said sensor is selected from the group consisting of a spectrophotometer, a Fabry-Perot spectrophotometer, a colorimeter, a low-cost LED (LCLED) color sensor, and a Full-Width-Array RGB scanner.

* * * * *